United States Patent

Krause et al.

Patent Number: 5,973,040
Date of Patent: Oct. 26, 1999

[54] TETRAMETHYLPIPERIDINE-CONTAINING COPOLYMERS

[75] Inventors: Alfred Krause, Speyer; Alexander Aumüller, Neustadt; Hubert Trauth, Dudenhofen; Albin Berger, Bobenheim; Andreas Deckers, Flomborn, all of Germany

[73] Assignee: BASF Aktiengesellschaft, Ludwigshafen, Germany

[21] Appl. No.: 09/077,296

[22] PCT Filed: Nov. 18, 1996

[86] PCT No.: PCT/EP96/05068

§ 371 Date: May 29, 1998

§ 102(e) Date: May 29, 1998

[87] PCT Pub. No.: WO97/19922

PCT Pub. Date: Jun. 5, 1997

[30] Foreign Application Priority Data

Nov. 29, 1995 [DE] Germany .................. 195 44 043

[51] Int. Cl.⁶ .................................................. C08K 5/3435
[52] U.S. Cl. ............................ 524/103; 524/99; 524/102; 526/258
[58] Field of Search ............................ 526/258; 524/103, 524/99, 102

[56] References Cited

U.S. PATENT DOCUMENTS

| | | | |
|---|---|---|---|
| 4,210,612 | 7/1980 | Karrer | 526/258 |
| 4,215,028 | 7/1980 | Mizuguchi et al. | 526/258 |
| 4,294,949 | 10/1981 | Karrer | 526/258 |
| 4,413,096 | 11/1983 | Fu et al. | |
| 4,450,224 | 5/1984 | Klein et al. | 526/258 |
| 5,434,202 | 7/1995 | Krause et al. | |
| 5,504,211 | 4/1996 | Aumueller et al. | |
| 5,624,981 | 4/1997 | Holderbaum et al. | |

*Primary Examiner*—Bernard Lipman
*Assistant Examiner*—N. Sarofim
*Attorney, Agent, or Firm*—Oblon, Spivak, McClelland, Maier & Neustadt, P.C.

[57] ABSTRACT

A description is given of tetramethylpiperidine-containing copolymers comprising 1–100 mol % of identical or different monomer units of the general formula I

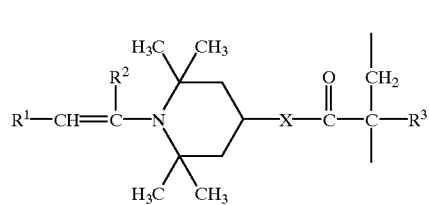

($R^1$=COOR⁷, COR⁸, CONR⁸R⁹, CN; $R^2$=H, $C_1$–$C_{12}$-alkyl, COOR⁷, COR⁸, CONR⁸R⁹, CN; $R^3$=H, methyl, ethyl, propyl; $R^6$=H, $C_1$–$C_8$-alkyl; $R^7$=H, $C_1$–$C_8$-alkyl, $C_5$–$C_8$-cycloalkyl, $C_3$–$C_5$-alkenyl, substituted or unsubstituted phenyl; $R^8$ and $R^9$=H, $C_1$–$C_{12}$-alkyl, $C_5$–$C_8$-cycloalkyl, substituted or unsubstituted phenyl; X=oxygen, sulfur, NR⁶) and also other monomers, and also of processes for preparing the copolymers, of the use of the copolymers as stabilizers, including light stabilizers, and of organic material comprising the copolymers.

11 Claims, No Drawings

TETRAMETHYLPIPERIDINE-CONTAINING COPOLYMERS

The present invention relates to tetramethylpiperidine-containing copolymers comprising I) 1–100 mol % of identical or different monomer units of the general formula I

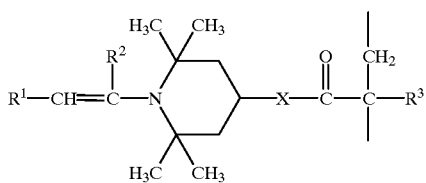

and

II) 0–99 mol % of identical or different monomer units of the general formula II

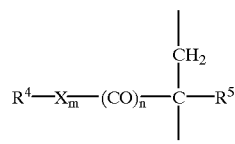

where

X is oxygen, sulfur or $NR^6$, $R^1$ is $COOR^7$, $COR^8$, $CONR^8R^9$ or CN, $R^2$ is hydrogen, $C_1$–$C_{12}$-alkyl, $COOR^7$, $COR^8$, $CONR^8R^9$ or CN, $R^3$ is hydrogen, methyl, ethyl or propyl, $R^4$ is hydrogen, straight-chain or branched $C_1$–$C_{20}$-alkyl, every third chain carbon being replaceable by oxygen or $NR^6$, or is $C_3$–$C_8$-cycloalkyl, phenyl or

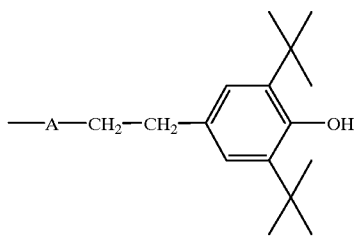

or

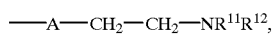

$R^5$ is hydrogen, methyl, ethyl or propyl, $R^6$ is hydrogen or $C_1$–$C_8$-alkyl, $R^7$ is hydrogen, $C_1$–$C_8$-alkyl, $C_5$–$C_8$-cycloalkyl, $C_3$–$C_5$-alkenyl or phenyl which can be substituted by 1–3 $C_1$–$C_4$-alkyls, $C_1$–$C_4$-alkoxys, $C_1$–$C_4$-alkoxycarbonyls, halogens, hydroxyls, phenoxys, phenyls, tolyls or xylyls, $R^8$ and $R^9$ are hydrogen, $C_1$–$C_{12}$-alkyl, $C_5$–$C_8$-cycloalkyl or phenyl which can be substituted by 1–3 $C_1$–$C_4$-alkyls, $C_1$–$C_4$-alkoxys, $C_1$–$C_4$-alkoxycarbonyls, halogens, hydroxyls, phenoxys, phenyls, tolyls or xylyls, $R^{10}$ is hydrogen or methyl, $R^{11}$ and $R^{12}$ are $C_1$–$C_4$-alkyl, A is a bridge member of the formula

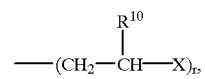

m and n are 0 or 1 and r is 0–100.

The invention additionally relates to processes for preparing the compounds, to the use of the copolymers as stabilizers and to organic material comprising the copolymers which is stabilized against the action of light, oxygen and heat.

Organic material, especially plastics and coating materials, is destroyed very rapidly by light, oxygen and heat, as is manifested for example in yellowing, discoloration, embrittlement or cracking. The intention of stabilizers is to prevent this destruction and to achieve extensive protection of the organic material against these damaging effects.

Among stabilizers, compounds with hindered amine units, such as the tetramethylpiperidine structure, have proven particularly suitable. Particularly advantageous tetramethylpiperidine compounds, in turn, are those having two or more piperidine radicals, for example dimeric or polymeric structures, since such compounds are diffused out of the stabilized organic material only with difficulty and therefore exhibit a particularly long-term protective effect.

U.S. Pat. No. 4,413,096 describes α-olefin copolymers with side chains which comprise tetraalkylpiperidine radicals, which radicals can be substituted on the nitrogen by hydrogen, oxyl, $C_1$–$C_8$-alkyl, $C_3$–$C_8$-alkenyl, $C_3$–$C_6$-alkynyl, $C_7$–$C_8$-aralkyl, —$CH_2CN$, $C_2$–$C_{21}$-alkoxyalkyl, aliphatic $C_1$–$C_4$-acyl, —$CH_2COOR$ or —COOR in which R can again be various organic radicals.

A frequent point of dissatisfaction in such prior art compositions is the low compatibility with plastics, the duration of the protective effect, the inherent color of the compounds, their low resistance to decomposition when incorporated at elevated temperatures and, in particular, their sensitivity to acidic, sulfur- and halogen-containing solids, liquids and gases.

It is an object of the present invention to provide stabilizers for organic material which provide more effective protection against light, oxygen and heat, especially in combination with improved protection against acidic liquids and gases.

We have found that this object is achieved by the tetramethylpiperidine-containing copolymers described at the outset.

A preferred bridge member X is oxygen.

A preferred radical $R^1$ is $COOR^7$.

$R^2$ is preferably hydrogen or $COOR^7$.

$R^3$ and $R^5$ are preferably hydrogen or methyl.

$R^4$ is preferably hydrogen, methyl, phenyl or

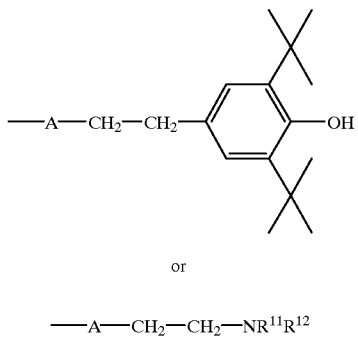

or

—A—CH$_2$—CH$_2$—NR$^{11}$R$^{12}$

The latter two radicals $R^4$ are particularly preferred when m and n are 1 and X is oxygen or $NR^6$.

$R^6$ is preferably hydrogen, methyl or ethyl.

$R^7$ is preferably $C_1$–$C_4$-alkyl, especially ethyl.

Examples of suitable radicals $R^2$, $R^4$, $R^6$, $R^7$, $R^8$, $R^9$, $R^{11}$ and $R^{12}$ are methyl, ethyl, n-propyl, isopropyl, n-butyl, isobutyl, sec-butyl and tert-butyl.

Suitable radicals $R^2$, $R^4$, $R^6$, $R^7$, $R^8$ and $R^9$ are additionally n-pentyl, isopentyl, sec-pentyl, tert-pentyl, neopentyl, n-hexyl, n-heptyl, n-octyl and 2-ethylhexyl.

Suitable radicals $R^2$, $R^4$, $R^2$ and $R^9$ are additionally n-nonyl, isononyl, n-decyl, n-undecyl and n-dodecyl.

Suitable radicals $R^4$, $R^7$, $R^8$ and $R^9$ are also cycloalkyls, especially cyclopentyl, cyclohexyl, cycloheptyl, cyclooctyl, methylcyclopentyl, dimethylcyclopentyl, methylcyclohexyl, dimethylcyclohexyl and ethylcyclohexyl.

$R^4$ can also be cyclopropyl or cyclobutyl.

$R^7$ is also suitably $C_3$–$C_5$-alkenyl, especially allyl, methallyl, crotyl, pentenyl, 1,3- and 2,4-pentadienyl.

The effective stabilizer unit present in the novel copolymers is the tetramethylpiperidine radical. This is particularly easy to obtain and has particularly advantageous properties. Very similar properties are also shown, however, by other tetraalkylpiperidine radicals in which one or more methyls have been replaced by other alkyls such as ethyl, propyl, butyl, or each two adjacent methyls are joined to form a cyclic radical.

Among the novel copolymers, preference is given to those in which the sum of monomer units I and II derived from acrylate or methacrylate, ie. in which m and n are 1 and $R^5$ and $R^3$ are hydrogen or methyl, is between 1 and 80 mol %, based on the total amount of monomer units in the copolymer. Particularly preferred copolymers are those in which this proportion is between 1 and 50 mol %.

The copolymers preferably have a mean molecular weight (weight average) of between 1000 and 50,000 daltons, in particular between 1000 and 25,000 daltons.

The novel copolymers can advantageously be prepared by polymer-analogous reactions in which, for example, a copolymer of I) 1–100 mol % of identical or different monomer units of the general formula Ia

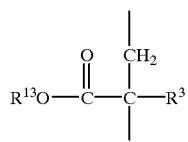

where $R^{13}$ is hydrogen, methyl, ethyl, propyl, butyl or dimethylaminoethyl and II) 0–99 mol % of identical or different monomer units of the general formula II is reacted polymer-analogously with a compound of the general formula III

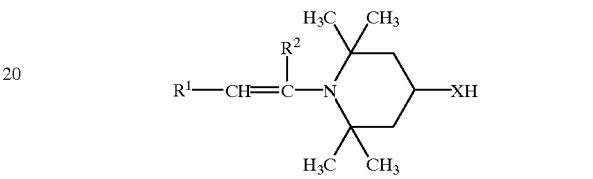

in the melt or in an inert high-boiling solvent with removal of the volatile reaction products.

The starting copolymer contains preferably 1–80 mol % of component Ia, particularly preferably 1–50 mol % and 99–20 mol %, particularly preferably 99–50 mol %, of component II, the latter then consisting of monomers in which m or n is 0. Component Ia is derived from an acrylic ester in which the alcohol residue $R^{13}$ is preferably methyl or ethyl but can also be hydrogen or dimethylaminoethyl.

The polymer-analogous reaction takes place in a manner known per se, preferably by azeotropic esterification or amidation, the water of reaction formed or the alcohol $R^{13}OH$ liberated being removed from the reaction mixture by distillation. For azeotropic esterification or amidation, an inert, high-boiling entrainer is added to the mixture of starting materials and is distilled off together with the water or alcohol. The entrainer can then be separated, for example, from the water and recycled to the reaction mixture. In this case a relatively small quantity of added entrainer, 50–200% by weight based on the expected quantity of water, is sufficient. Without recycling, up to a 30-fold excess of entrainer is generally added, and can also be added continuously.

Examples of suitable entrainers are toluene, xylene, cyclohexane, methylcyclohexane or commercially available mixtures of aromatic hydrocarbons. Toluene is preferably employed.

The distillation temperature depends both on the boiling point of the entrainer or azeotrope and on the reaction pressure. Distillation can be carried out at atmospheric pressure but is preferably performed under a reduced pressure of eg. 50–400 mbar. The temperature is generally between 100 and 250° C., particularly preferably 150–200° C.

The polymer-analogous reaction can also be carried out in the melt, for example in a compounder or extruder. The choice of temperature depends principally on the melting point of the starting polymer. The reaction is generally carried out at 80–300° C., preferably 120–250° C., advantageously with distillation under reduced pressure, eg. 50–400 mbar. As in solution, reaction in the melt can also be operated continuously or batchwise.

The reaction is preferably carried out in the presence of a catalyst. Examples of suitable catalysts are protic acids such as p-toluenesulfonic acid, sulfuric acid, phosphoric acid, Lewis acids, such as tetraalkyl titanates or organotin compounds, or basic compounds such as alkaline earth metal hydroxides and alkaline earth metal carbonates, and also lithium amide and sodium amide.

The preparation of compounds III is described for example in DE-A 4140304 or can be carried out by the methods described therein.

The synthesis of copolymers of 1-olefins and acrylic acid erivatives is described for example in Houben-Weyl, Methoden der rganischen Chemie, Volume XIV/1.

The novel copolymers are outstandingly suitable for stabilizing organic material against the action of light, oxygen and heat, especially under the simultaneous action of acidic liquids or gases.

The term organic material is intended to include, for example, cosmetic preparations such as ointments and lotions, pharmaceutical formulations such as tablets and suppositories, photographic recording materials, especially photographic emulsions, or precursors for plastics and coating materials, but especially plastics and coating materials themselves.

The present invention additionally relates to organic material, especially plastics and coating materials, stabilized against the action of light, oxygen and heat and comprising 0.01–5% by weight, preferably 0.02–1% by weight, based on the total weight of organic material, of one or more novel copolymers.

For mixing the novel copolymers with, in particular, plastics it is possible to employ all known devices and methods for mixing stabilizers or other additives into polymers.

The organic material stabilized by the novel copolymers may include other additives, eg. antioxidants, light stabilizers, metal passivators, antistats, flame retardants, pigments and fillers.

Antioxidants and light stabilizers which can be added besides the novel compounds are, for example, compounds based on sterically hindered phenols, or costabilizers comprising sulfur or phosphorus.

Examples of such phenolic antioxidants are 2,6-di-tert-butyl-4-methylphenol, n-octadecyl β-(3,5-di-tert-butyl-4-hydroxyphenyl)propionate, 1,1,3-tris(2-methyl-4-hydroxy-5-tert-butyl-phenyl)butane, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 1,3,5-tris[β-(3,5-di-tert-butyl-4-hydroxyphenyl)propionylethyl]isocyanurate, 1,3,5-tris(2,6-dimethyl-3-hydroxy-4-tert-butylbenzyl) isocyanurate and pentaerythritol tetrakis[β-(3,5-di-tert-butyl-4-hydroxyphenyl)propionate].

Examples of phosphorus-containing antioxidants are tris (nonylphenyl) phosphite, distearyl pentaerythritol diphosphite, tris(2,4-di-tert-butyl-phenyl) phosphite, tris(2-tert-butyl-4-methylphenyl) phosphite, bis(2,4-di-tert-butylphenyl) pentaerythritol diphosphite and tetrakis(2,4-di-tert-butylphenyl) 4,4'-biphenylenediphosphite.

Examples of sulfur-containing antioxidants are dilauryl thiodipropionate, dimyristyl thiodipropionate, distearyl thiodipropionate, pentarythritol tetrakis(β-laurylthiopropionate) and pentaerythritol tetrakis(β-hexylthiopropionate).

Other antioxidants and light stabilizers which can be used together with the novel copolymers include eg. 2-(2'-hydroxyphenyl)benzotriazoles, 2-hydroxybenzophenones, aryl esters of hydroxybenzoic acids, α-cyanocinnamic acid derivatives, benzimidazolecarboxanilides, nickel compounds or oxalanilides.

Examples of plastics which can be stabilized by the novel copolymers are:

polymers of mono- and diolefins, for example low- or high-density polyethylene, polypropylene, linear poly-1-butene, polyisoprene, polybutadiene and copolymers of mono- or diolefins or mixtures of these polymers;

copolymers of mono- or diolefins with other vinyl monomers, for example ethylene-alkyl acrylate, ethylene-alkyl methacrylate, ethylene-vinyl acetate or ethylene-acrylic acid copolymers;

polystyrene and copolymers of styrene or a-methylstyrene with dienes and/or acrylic derivatives, for example styrene-butadiene, styrene-acrylonitrile (SAN), styrene-ethyl methacrylate, styrene-butadiene-ethyl acrylate, styrene-acrylonitrile-methacrylate, acrylonitrile-butadiene-styrene (ABS) or methyl methacrylate-butadiene-styrene (MBS);

halogen-containing polymers, for example polyvinyl chloride, polyvinyl fluoride, polyvinylidene fluoride and copolymers thereof;

Polymers derived from α,β-unsaturated acids and derivatives thereof, such as polyacrylates, polymethacrylates, polyacrylamides and polyacrylonitriles;

polymers derived from unsaturated alcohols and amines or their acyl derivatives or acetals, for example polyvinyl alcohol and polyvinyl acetate;

polyurethanes, polyamides, polyureas, polyesters, polycarbonates, polysulfones, polyether sulfones and polyether ketones.

With the novel copolymers it is also possible to stabilize coating films, for example industrial coatings. Among these particular emphasis should be placed on stoving finishes, which in turn include automotive finishes, preferably two-coat finishes. Examples of other applications are coating compositions for exterior masonry paints, other constructions or industrial equipment.

The novel copolymers can be added in solid or liquid form to the coating material. In this context, their ready solubility in coating systems is a particular advantage.

The novel compounds I are notable for high compatibility with the customary types of plastic and by good solubility in and excellent compatibility with the customary coating systems. In general they are devoid of, or have only a slight, inherent color, are stable at customary plastics and coatings processing temperatures, are not volatile and above all provide for a long period of protection of the materials treated with them.

EXAMPLES

Polymer-analogous reaction of N,N-dimethylaminoethyl acrylate-ethylene copolymers with ethyl β-(2,2,6,6-tetramethyl-4-hydroxy-1-piperidyl) acrylate (IV)

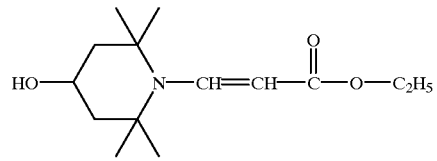

IV 20 g of N,N-dimethylaminoethyl acrylate-ethylene copolymer with the proportion of acrylate indicated in Table 1 (in mol % based on the total amount of monomers in the copolymer) were heated with different amounts of IV (see Table 1) in the presence of 0.5 g of p-toluenesulfonic acid as catalyst at 210–220° C. for 4 hours. During this time, the N,N-dimethylaminooctanol formed was distilled off and the volume of distillate was used to determine the acrylate conversion (see Table 1). (The copolymers employed had different molecular weights. The viscosity at 120° C. was determined as a parameter of their size, and is likewise indicated in Table 1.)

TABLE 1

| Example | Viscosity of the copolymer [mPas] | Acrylate content of the copolymer [mol %] | Volume of distillate [ml] | Amount of IV used [g] | Conversion of acrylate groups [%] |
|---|---|---|---|---|---|
| 1 | 1100 | 18.0 | 3.0 | 25 | >90 |
| 2 | 1100 | 18.0 | 1.4 | 12 | 50 |
| 3 | 5000 | 13.0 | 2.4 | 25 | >90 |
| 4 | 5000 | 13.0 | 1.4 | 12 | 60 |
| 5 | 2080 | 12.0 | 3.5 | 25 | >90 |
| 6 | 2080 | 12.0 | 1.5 | 12 | 50 |
| 7 | 1600 | 12.6 | 3.5 | 25 | >90 |
| 8 | 1600 | 12.6 | 1.4 | 12 | 50 |

Polymer-analogous reaction of acrylic acid-ethylene copolymers with IV without entrainers.

Similarly to Examples 1–8, 73 g of IV were reacted in each case with 100 g of different acrylic acid-ethylene copolymers in the presence of 0.5 g of different catalysts (see Table 2), with the ater of reaction formed being distilled off. After cooling, the solidified reaction mixture was ground and subjected to continuous hot extraction with methanol. The residue was dried at 50° C. in vacuo. The results (conversion of acrylic groups, elemental analysis) are shown in Table 2.

TABLE 2

| Example | Viscosity of the copolymer [mPas] | Acrylate content of the copolymer [mol %] | Catalyst | Conversion of the acrylic group [%] | Elemental analysis [% C; % H; % O; % N] |
|---|---|---|---|---|---|
| 9 | 30,000 | 20.0 | Dibutyltin diacetate | 90 | 75.2; 11.4; 10.7; 1.8 |
| 10 | 30,000 | 20.0 | conc. $H_2SO_4$ | 80 | 75.0; 11.7; 10.7; 1.6 |
| 11 | 30,000 | 20.0 | p-toluene sulfonic acid | 80 | 75.4; 11.9; 10.4; 1.6 |

Polymer-analogous reaction of acrylic acid-ethylene copolymers with IV in the presence of an entrainer:

50 g of various acrylic acid-ethylene copolymers were heated at boiling for 10 hours with 38.3 g of IV and 0.5 g of catalyst in 150 ml of an aromatic hydrocarbon mixture having a boiling point of about 150° C., the distillate being separated into water and entrainer and the entrainer being recycled to the reaction mixture. After cooling, the mixture was stirred into methanol. The precipitated product was filtered off with suction, washed twice with methanol and dried at 50° C. in vacuo. The results are shown in Table 3.

TABLE 3

| Example | Viscosity of the copolymer [mPas] | Acrylate content of the copolymer [mol %] | Catalyst | Conversion of the acrylic group [%] | Elemental analysis [% C; % H; % O; % N] |
|---|---|---|---|---|---|
| 12 | 10,000 | 18.7 | Dibutyltin diacetate | 50 | 75.7; 11.8; 9.4; 1.5 |
| 13 | 500 | 57.0 | Dibutyltin diacetate | 80 | 70.8; 10.5; 13.9; 3.9 |
| 14 | 30,000 | 20.0 | conc. $H_2SO_4$ | 85 | 74.9; 11.8; 10.1; 1.8 |
| 15 | 30,000 | 20.0 | p-toluenesulfonic acid | 90 | 75.1; 11.7; 10.5; 2.2 |
| 16 | 30,000 | 20.0 | SnO | 80 | 75.8; 12.2; 9.1; 1.0 |

Example 17

Similarly to Example 3, a corresponding copolymer was reacted with 4-hydroxy-2,2,6,6-tetramethylpiperidine (comparison sample).

0.1% by weight of each of the tetramethylpiperidine-containing copolymers of Example 3 and Example 17 (comparison sample) was incorporated into low-density polyethylene by single extrusion. The resulting granules were processed to give 250 μm films. Sections of these films were subjected to a rapid weathering test (Xenotest 1200 apparatus). The time was measured until embrittlement (cracking) of the test specimens.

| Test specimens | Hours before cracking |
|---|---|
| Film with stabilizer acc. to Ex. 3 | 6000–6500 |
| Film with stabilizer acc. to Ex. 17 | 4500–5000 |

We claim:

1. A tetramethylpiperidine-containing copolymer comprising

I) 1–100 mol % of identical or different monomer units of the general formula I

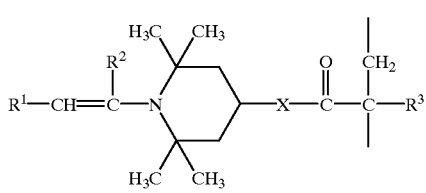

and

II) 0–99 mol % of identical or different monomer units of the general formula II

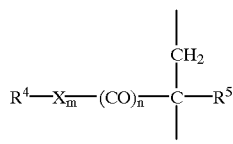

where
X is oxygen, sulfur or $NR^6$,
$R^1$ is $COOR^7$, $COR^8$, $CONR^8R^9$ or CN,
$R^2$ is hydrogen, $C_1$–$C_{12}$-alkyl, $COOR^7$, $COR^8$, $CONR^8R^9$ or CN,
$R^3$ is hydrogen, methyl, ethyl or propyl,
$R^4$ is hydrogen, straight-chain or branched $C_1$–$C_{20}$-alkyl, every third chain carbon being replaceable by oxygen or $NR^6$, or is $C_3$–$C_8$-cycloalkyl, phenyl or

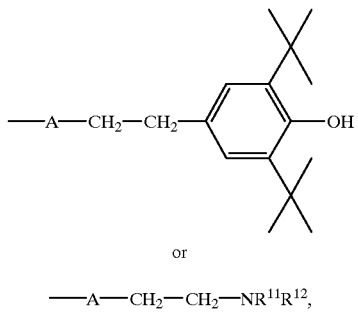

or

—A—$CH_2$—$CH_2$—$NR^{11}R^{12}$, $R^5$ is hydrogen, methyl, ethyl or propyl,
$R^6$ is hydrogen or $C_1$–$C_8$-alkyl,
$R^7$ is hydrogen, $C_1$–$C_8$-alkyl, $C_5$–$C_8$-cycloalkyl, $C_3$–$C_5$-alkenyl or phenyl which can be substituted by 1–3 $C_1$–$C_4$-alkyls, $C_1$–$C_4$-alkoxys, $C_1$–$C_4$-alkoxycarbonyls, halogens, hydroxyls, phenoxys, phenyls, tolyls or xylyls,
$R^8$ and $R^9$ are hydrogen, $C_1$–$C_{12}$-alkyl, $C_5$–$C_8$-cycloalkyl or phenyl which can be substituted by 1–3 $C_1$–$C_4$-alkyls, $C_1$–$C_4$-alkoxys, $C_1$–$C_4$-alkoxycarbonyls, halogens, hydroxyls, phenoxys, phenyls, tolyls or xylyls,
$R^{10}$ is hydrogen or methyl,
$R^{11}$ and $R^{12}$ are $C_1$–$C_4$-alkyl,
A is a bridge member of the formula

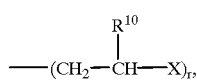

m and n are 0 or 1 and
r is 0–100.

2. A copolymer as claimed in claim 1, wherein $R^1$ is $COOR^7$.

3. A copolymer as claimed in claim 1, wherein $R^2$ is hydrogen or $COOR^7$.

4. A copolymer as claimed in claim 1, wherein $R^7$ is $C_1$–$C_4$-alkyl.

5. A copolymer as claimed in any one of claim 1, wherein in some of the monomer units II X is oxygen or $NR^6$, m and n are 1 and $R^4$ is

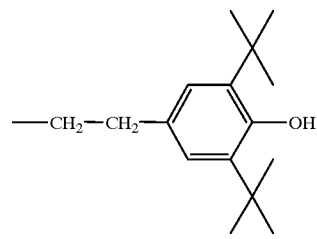

or

—$CH_2$—$CH_2$—$N(CH_3)_2$

6. A copolymer as claimed in claim 1, wherein the sum of monomer units I and II derived from acrylate or methacrylate is between 1 and 80 mol %, based on the total amount of monomer units in the copolymer.

7. A copolymer as claimed in claim 1, having a mean molecular weight (weight average) of between 1000 and 50,000 daltons.

8. A process for preparing a copolymer as claimed in claim 1, by reacting a copolymer comprising
 I) 1–100 mol % of identical or different monomer units of the general formula Ia

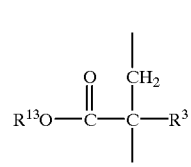

where $R^{13}$ is hydrogen, methyl, ethyl, propyl, butyl or dimethylaminoethyl and
II) 0–99 mol % of identical or different monomer units of the general formula II
polymer-analogously with a compound of the general formula III

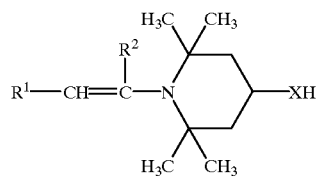

in the melt or in an inert high-boiling solvent with removal of the volatile reaction products.

9. An organic material which is stabilized against the action of light, oxygen and heat and comprises 0.01–5% by weight, based on the total amount of organic material, of one or more tetramethylpiperidine-containing copolymers as claimed in claim 1.

10. A plastic or coating material which is stabilized against the action of light, oxygen and heat and comprises 0.01–5% by weight, based on the total amount of organic material, of one or more tetramethylpiperidine-containing copolymers as claimed in claim 1.

11. A method of stabilizing an organic material comprising adding to the organic material the copolymer as claimed in claim 1 in an amount effective to stabilize the organic material.

* * * * *

UNITED STATES PATENT AND TRADEMARK OFFICE
CERTIFICATE OF CORRECTION

PATENT NO. : 5,973,040

DATED : October 26, 1999

INVENTOR(S): Alfred KRAUSE, et al.

It is certified that an error appears in the above-identified patent and that said Letters Patent is hereby corrected as shown below:

On the title page, item [30] should be:

--[30]    Foreign Application Priority Data
    Nov. 29, 1995 [DE] Germany ........... 195 44 404--

Signed and Sealed this

Thirteenth Day of February, 2001

Attest:

NICHOLAS P. GODICI

Attesting Officer    Acting Director of the United States Patent and Trademark Office